United States Patent
Ertel et al.

(10) Patent No.: US 7,581,885 B2
(45) Date of Patent: Sep. 1, 2009

(54) METHOD AND SYSTEM OF ALIGNING X-RAY DETECTOR FOR DATA ACQUISITION

(75) Inventors: Jason R. Ertel, Waukesha, WI (US); John R. Lamberty, Oconomowoc, WI (US)

(73) Assignee: General Electric Company, Schenectady, NY (US)

( * ) Notice: Subject to any disclaimer, the term of this patent is extended or adjusted under 35 U.S.C. 154(b) by 845 days.

(21) Appl. No.: 10/904,728

(22) Filed: Nov. 24, 2004

(65) Prior Publication Data

US 2006/0109958 A1    May 25, 2006

(51) Int. Cl.
*A61B 6/08* (2006.01)
*H05G 1/00* (2006.01)

(52) U.S. Cl. .................. 378/206; 378/204; 378/205

(58) Field of Classification Search .................. 378/62, 378/195, 204–206
See application file for complete search history.

(56) References Cited

U.S. PATENT DOCUMENTS

| | | | |
|---|---|---|---|
| 5,103,092 A | 4/1992 | Takahashi et al. | |
| 5,262,871 A | 11/1993 | Wilder et al. | |
| 5,281,803 A | 1/1994 | Ishizuka | |
| 5,508,740 A | 4/1996 | Miyaguchi et al. | |
| 5,514,873 A | 5/1996 | Schulze-Ganzlin et al. | |
| 5,608,774 A | 3/1997 | Polichar et al. | |
| 5,661,309 A | 8/1997 | Jeromin et al. | |
| 5,693,948 A | 12/1997 | Sayed et al. | |
| 5,715,292 A | 2/1998 | Sayag et al. | |
| 5,773,832 A | 6/1998 | Sayed et al. | |
| 5,811,790 A | 9/1998 | Endo et al. | |
| 5,822,389 A | 10/1998 | Uzawa et al. | |
| 5,828,726 A | 10/1998 | Polichar et al. | |
| 5,903,052 A | 5/1999 | Chen et al. | |
| 5,909,478 A | 6/1999 | Polichar et al. | |
| 5,962,856 A | 10/1999 | Zhao et al. | |
| 5,965,872 A | 10/1999 | Endo et al. | |
| 6,022,143 A * | 2/2000 | Helmreich | 378/181 |
| 6,049,074 A | 4/2000 | Endo et al. | |
| 6,078,036 A * | 6/2000 | Cook et al. | 250/206.1 |
| 6,127,714 A | 10/2000 | Mochizuki | |
| 6,173,033 B1 * | 1/2001 | Klingenbeck-Regn et al. | 378/20 |
| 6,208,708 B1 | 3/2001 | Hoheisel et al. | |
| 6,232,607 B1 | 5/2001 | Huang | |
| 6,239,439 B1 | 5/2001 | Itabashi et al. | |
| 6,255,638 B1 | 7/2001 | Eräluoto et al. | |
| 6,266,142 B1 * | 7/2001 | Junkins et al. | 356/623 |

(Continued)

FOREIGN PATENT DOCUMENTS

JP    11271454    10/1999

(Continued)

*Primary Examiner*—Edward J Glick
*Assistant Examiner*—Anastasia Midkiff
(74) *Attorney, Agent, or Firm*—Ziolkowski Patent Solutions Group, SC

(57) ABSTRACT

A method and system of aligning an x-ray detector and x-ray tube for data acquisition are presented. The x-ray detector and x-ray tube are equipped with transmitters and receivers designed to provide feedback relating to the orientation, spacing, and general position thereof. In this regard, a user can effectively and efficiently position the x-ray tube and x-ray detector relative to one another for data acquisition.

21 Claims, 5 Drawing Sheets

U.S. PATENT DOCUMENTS

| | | | |
|---|---|---|---|
| 6,288,381 B1 * | 9/2001 | Messina | 250/201.1 |
| 6,323,891 B1 | 11/2001 | Kitani et al. | |
| 6,331,705 B1 | 12/2001 | Eisen et al. | |
| 6,333,963 B1 | 12/2001 | Kaifu et al. | |
| 6,344,652 B1 | 2/2002 | Shoji | |
| 6,375,354 B1 * | 4/2002 | Polkus et al. | 378/205 |
| 6,398,409 B1 | 6/2002 | Brooks | |
| 6,459,132 B1 | 10/2002 | Mochizuki | |
| 6,469,312 B2 | 10/2002 | Agano | |
| 6,475,824 B1 | 11/2002 | Kim | |
| 6,552,319 B2 | 4/2003 | Pyyhtiä et al. | |
| 6,667,480 B2 | 12/2003 | Kajiwara et al. | |
| 6,700,126 B2 | 3/2004 | Watanabe | |
| 6,707,880 B2 | 3/2004 | Yamayoshi | |
| 6,714,623 B2 | 3/2004 | Sako et al. | |
| 6,723,592 B2 | 4/2004 | Shih | |
| 2001/0056234 A1 * | 12/2001 | Weinberg | 600/436 |
| 2002/0005490 A1 | 1/2002 | Watanabe | |
| 2002/0150214 A1 | 10/2002 | Spahn | |
| 2002/0181659 A1 | 12/2002 | Watanabe et al. | |
| 2003/0031296 A1 | 2/2003 | Hoheisel | |
| 2004/0105526 A1 * | 6/2004 | Zhang et al. | 378/205 |
| 2005/0063512 A1 * | 3/2005 | Maschke | 378/91 |
| 2005/0129175 A1 * | 6/2005 | Shen et al. | 378/62 |

FOREIGN PATENT DOCUMENTS

| | | |
|---|---|---|
| JP | 2001099942 | 4/2001 |
| JP | 2001198116 | 7/2001 |
| JP | 2001224579 | 8/2001 |
| JP | 2002006049 | 1/2002 |
| JP | 2002014170 | 1/2002 |
| JP | 2002048873 | 2/2002 |
| JP | 2002125960 | 5/2002 |
| JP | 2002131437 | 5/2002 |
| JP | 2003000586 | 1/2003 |
| JP | 2003010175 | 1/2003 |
| JP | 2003014862 | 1/2003 |
| JP | 2003060181 | 2/2003 |
| JP | 2003334184 | 11/2003 |

* cited by examiner

METHOD AND SYSTEM OF ALIGNING X-RAY DETECTOR FOR DATA ACQUISITION

BACKGROUND OF THE INVENTION

The present invention relates generally to x-ray systems and, more particularly, to a method and system of aligning an x-ray detector such that the x-ray detector is perpendicular to and properly spaced from an x-ray tube during data acquisition.

X-ray imaging is a non-invasive technique to capture images of medical patients for clinical diagnosis as well as inspect the contents of sealed containers, such as luggage, packages, and other parcels. To capture these images, an x-ray source irradiates a scan subject with a fan beam of x-rays. The x-rays are then attenuated as they pass through the scan subject. The degree of attenuation varies across the scan subject as a result of variances in the internal composition of the subject. The attenuated energy impinges upon an x-ray detector designed to convert the attenuating energy to a form usable in image reconstruction. A control system reads out electrical charge stored in the x-ray detector and generates a corresponding image. For a conventional, screen film detector, the image is developed on a film and displayed using a backlight.

Increasingly, flat panel, digital x-ray detectors are being used to acquire data for image reconstruction. Flat panel detectors are generally constructed as having a scintillator which is used to convert x-rays to visible light that can be detected by a photosensitive layer. The photosensitive layer includes an array of photosensitive or detector elements that each store electrical charge in proportion to the light that is individually detected. Generally, each detector element has a light sensitive region and a region comprised of electronics to control the storage and output of electrical charge. The light sensitive region is typically composed of a photoconductor, and electrons are released in the photoconductor when exposed to visible light. During this exposure, charge is collected in each detector element and is stored in a capacitive element (diode) situated in the electronics region. After exposure, the charge in each detector element is read out using logic controlled electronics.

Each detector element is conventionally controlled using a transistor-based switch. In this regard, the source of the transistor is connected to the diode, the drain of the transistor is connected to a readout line, and the gate of the transistor is connected to a scan control interface disposed on the electronics in the detector. When negative voltage is applied to the gate, the switch is driven to an OFF state, i.e. no conduction between the source and drain. On the other hand, when a positive voltage is applied to the gate, the switch is turned ON resulting in connection of the source to the drain. Each detector element of the detector array is constructed with a respective transistor and is controlled in a manner consistent with that described below.

Specifically, during exposure to x-rays, negative voltage is applied to all gate lines resulting in all the transistor switches being driven to or placed in an OFF state. As a result, any charge accumulated during exposure is stored in each detector element capacitor. During read out, positive voltage is sequentially applied to each gate line, one gate at a time. In this regard, only one detector element is read out at a time. A multiplexer may also be used to support read out of the detector elements in a raster fashion. An advantage of sequentially reading out each detector element individually is that the charge from one detector element does not pass through any other detector elements. The output of each detector element is then input to a digitizer that digitizes the acquired signals for subsequent image reconstruction on a per pixel basis. Each pixel of the reconstructed image corresponds to a single detector element of the detector array.

As described above, for indirect detection, digital x-ray detectors utilize a layer of scintillating material, such as Cesium iodide (CsI), to convert incident radiation to visible light that is detected by light sensitive regions of individual detector elements of a detector array. Generally, the transistor controlled detector elements are supported on a thin substrate of glass. The substrate, which supports the detector elements as well as the scintillator layer, is supported by a panel support. The support panel is not only designed to support the detector components, but also isolates the electronics for controlling the detector from the detector components. The electronics are supported by the base of a cover assembly enclosing the internal components of the x-ray detector.

It is generally well-known that radiation detection efficiency and resulting image quality are, in part, a function of the orientation of the x-ray detector relative to the x-ray tube during data acquisition. In a cross-table x-ray scan, it is preferred that the plane of the x-ray detector be perpendicular to the plane of the beam of x-rays emitted by the x-ray tube. If the alignment of the x-ray detector and the x-ray tube are not generally perpendicular, dose may not be uniform across the x-ray detector yielding an image prone to artifacts. As a result, multiple x-ray images may be needed to reconstruct a diagnostically valuable image, which requires additional subject exposure to radiation and negatively affects subject throughput.

There is a general need to develop a system to assist a user in properly aligning an x-ray detector and an x-ray tube relative to one another. Presently, a user typically relies upon experience when positioning an x-ray detector and x-ray tube relative to one another. While for some x-ray scans this is feasible, when the x-ray detector and x-ray tube are to be positioned at an angle, achieving a proper alignment can be particularly difficult. As a result, a user must subject the subject to an x-ray scan, determine if the image is of sufficient image quality, and, if not, re-acquire data from the subject.

Therefore, it would be desirable to design a system and method of assisting a user in positioning an x-ray tube and x-ray scanner relative to one another.

BRIEF DESCRIPTION OF THE INVENTION

The present invention is a directed to a method and system of aligning an x-ray detector relative to an x-ray tube such that the x-ray detector and x-ray tube are properly spaced and oriented for data acquisition that overcome the aforementioned drawbacks.

The x-ray detector and x-ray tube are equipped with sensors that communicate to provide feedback as to the orientation of an x-ray tube and x-ray detector. In this regard, the present invention assists a user in properly aligning the x-ray detector and x-ray tube, e.g. perpendicular to one another. The x-ray detector is preferably equipped with multiple sensors that collectively form a point of convergence. When this point of convergence intersects a central axis extending perpendicularly from the x-ray tube, it is deemed that the detector and tube are properly oriented. On the other hand, the x-ray tube may be equipped with transceivers designed to emit multiple beams toward multiple sensors in the x-ray detector. When the sensors in the x-ray detector receive a corresponding beam from the x-ray tube transmitters, it is deemed that the detector is properly aligned relative to the x-ray tube. It is also possible to not only measure the incidence but also magnitude of a received signal to achieve a proper distance between the x-ray detector and x-ray tube for data acquisition.

Therefore, in accordance with one aspect, the present invention includes an x-ray detector having a scintillator designed to output light in response to reception of x-rays and a detector element array configured to detect light output from the scintillator and output electrical signals indicative of the x-rays received by the scintillator for image reconstruction. The x-ray detector also has a plurality of electronic position sensors configured to provide feedback as to a position of the scintillator relative to an x-ray source.

In accordance with another aspect, the present invention includes an x-ray imaging system. The system includes an x-ray source configured to provide a beam of x-rays at a subject to be imaged and a positionable x-ray detector configured to detect x-rays attenuated by the subject. The imaging system further includes a controller configured to electronically determine an orientation of the positionable x-ray detector relative to the x-ray source such that the positionable x-ray detector is substantially perpendicular to the beam of x-rays during imaging of the subject.

According to another aspect, the present invention includes an x-ray detector having means for converting x-rays into electrical signals capable of being processed for reconstruction of an image and means for electronically determining orientation of the converting means relative to an x-ray source such that the converting means is substantially perpendicular to an x-ray beam during data acquisition.

Various other features and advantages of the present invention will be made apparent from the following detailed description and the drawings.

BRIEF DESCRIPTION OF THE DRAWINGS

The drawings illustrate one preferred embodiment presently contemplated for carrying out the invention.

In the drawings.

DETAILED DESCRIPTION OF THE PREFERRED EMBODIMENT

The present invention will be described with respect to a flat panel, solid-state, indirect detection, portable digital x-ray detector for use with a mobile x-ray imaging system. However, the present invention is equivalently applicable with other types of x-ray detectors including direct detection digital detectors. Additionally, the present invention may be used with stationary or fixed room x-ray imaging systems. Further, the present application makes reference to an imaging "subject" as well as an imaging "object". The terms are interchangeable and are not intended to limit the scope of the appending claims.

Figure 1:
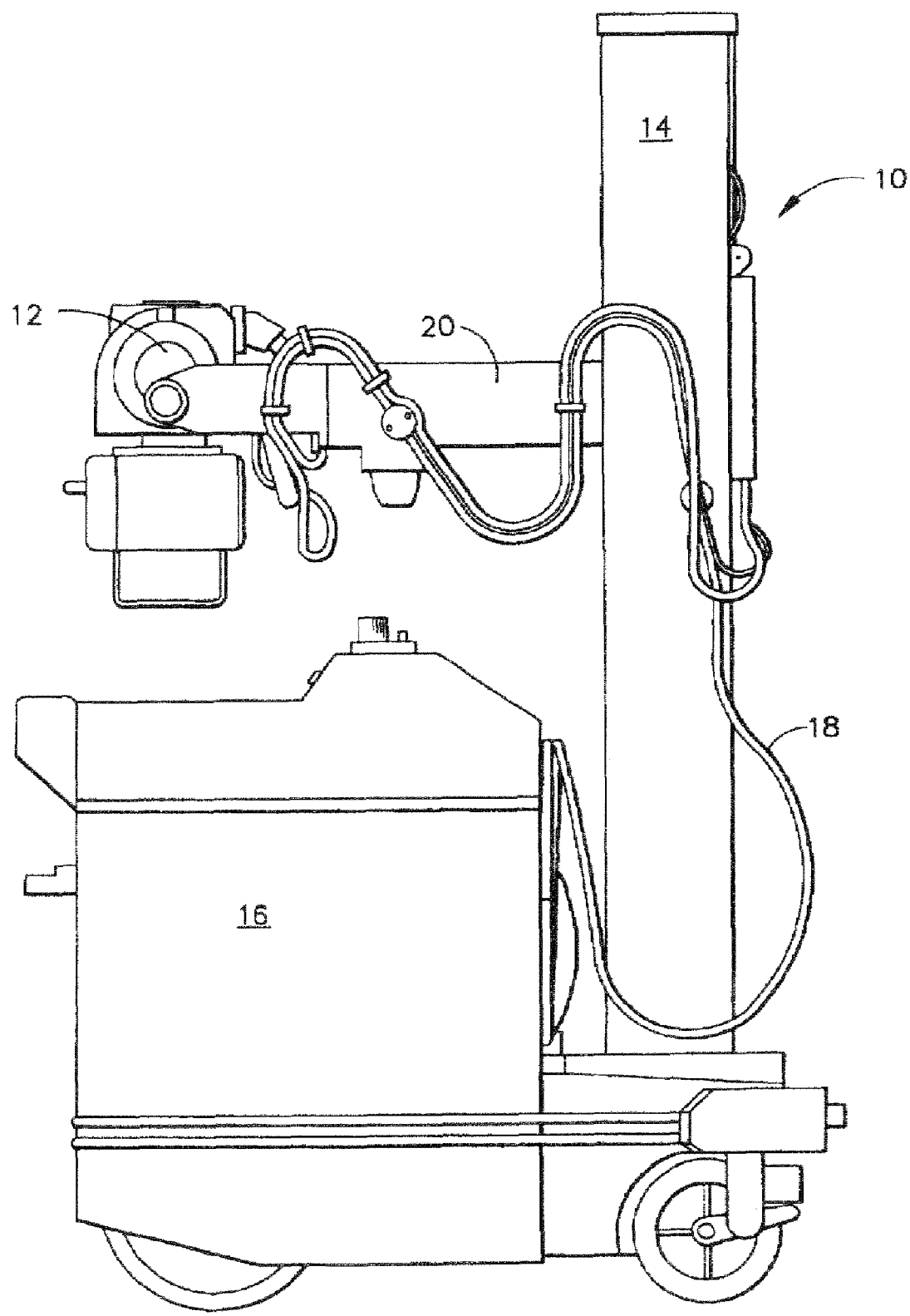
FIG. 1 is a pictorial view of an exemplary mobile x-ray imaging system.

Referring now to FIG. 1, an exemplary mobile x-ray imaging system 10 applicable with a portable x-ray detector incorporating the present invention is shown. An x-ray source 12 is mounted or otherwise secured to an end of horizontal arm 20. Arm 20 allows the x-ray source 12 to be variably positioned above a subject in such a manner so as to optimize irradiation of a particular area of interest. The x-ray source 12 is typically mounted through a gimbal-type arrangement (not shown) in column 14. In this regard, the x-ray source may be rotated vertically from a rest or park position on the mobile x-ray unit base 16 to the appropriate position above the subject in order to take an x-ray exposure of the subject. The rotational movement of column 14 is typically limited to a value of 360 degrees or less to prevent entanglement of high voltage cables 18 used to provide electrical power to the x-ray source 12. Cables 18 may be connected to a utility line source (not shown) or a battery (not shown) in the base 16 to energize the x-ray source 12 as well as other electronic components of the system 10. One skilled in the art will appreciate that system 10 may be equipped or connectable to a display unit (not shown) for the display of images captured from the imaging subject.

Figure 2:
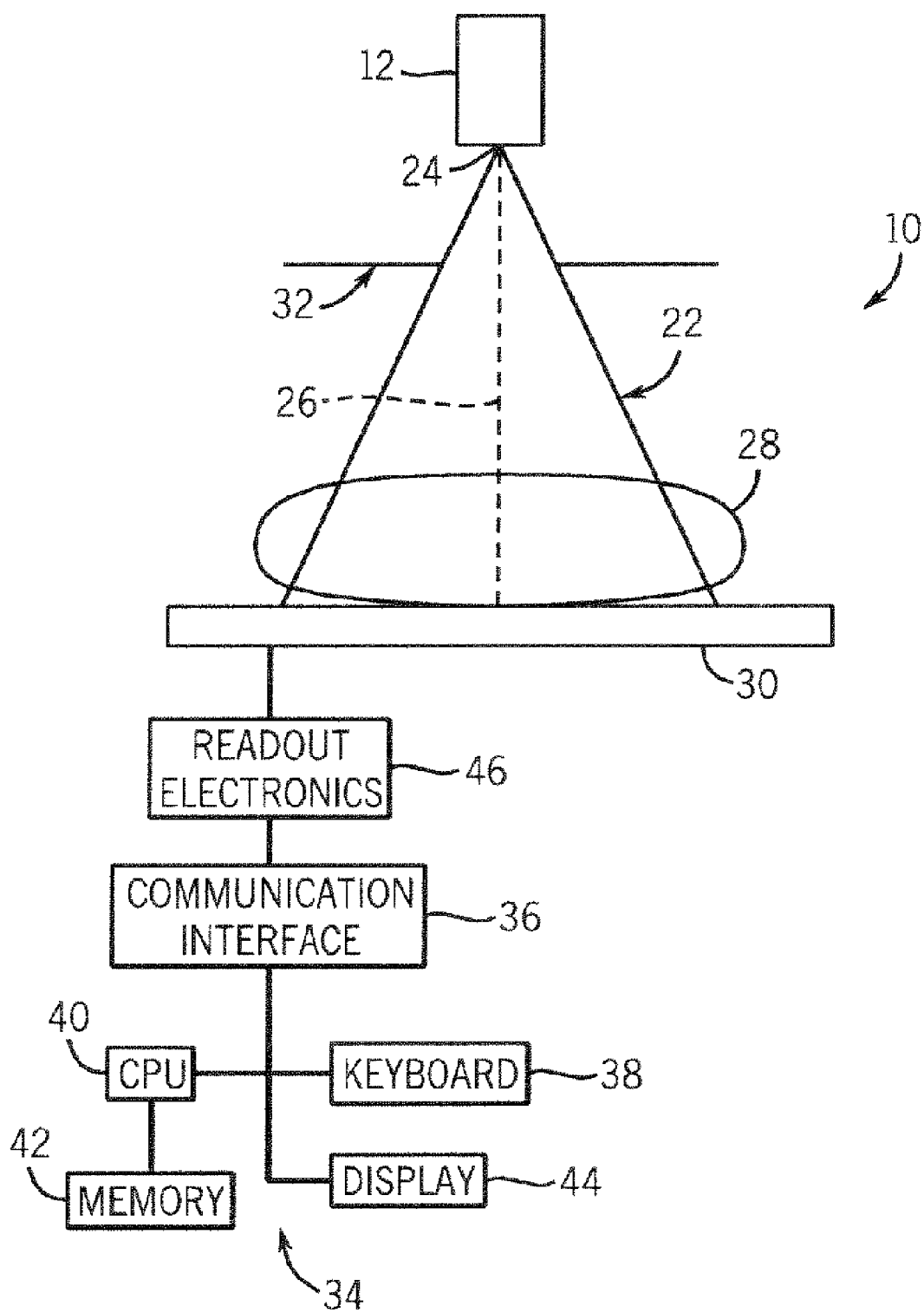
FIG. 2 is a schematic block diagram of the exemplary x-ray imaging system shown in FIG. 1.

Referring now to FIG. 2, a schematic of x-ray imaging system 10 is illustrated. As referenced above, system 10 includes x-ray source 12 designed to project a fan beam of irradiation 22 from focal spot 24 along axis 26 toward an object to be imaged 28. One skilled in the art will appreciate that medical patients as well as luggage, packages, and the like may be non-invasively inspected using the exemplary x-ray imaging system 10. A flat panel digital detector 30 detects x-rays passing through and attenuated by object 28. A collimator assembly 32, schematically shown in FIG. 2 as comprising collimator blades, may be used to collimate the x-ray fan beam 22 to control the scope of irradiation.

A host or scanner interface 34 includes a communication interface 36, a keyboard 38 or other data entry device, a CPU 40, memory 42, and a display unit 44, such a computer monitor, to display reconstructed images of the object. A bus 46 connects the keyboard 38, CPU 40, memory 42, and display unit 44 to the communication interface 36. The CPU may include a microprocessor, digital signal processor, microcontroller, as well as other devices designed to carry out logic and processing operations. Signals corresponding to an x-ray image are read out from flat panel detector 30 via readout electronics 46. While not shown, it is contemplated that the host interface 34 may be connected to a centralized facility via the Internet or communications link for monitoring and maintenance.

Additionally, the readout electronics may read out signals from the flat panel detector across a tethered connection between the detector and the imaging system. It is also contemplated that read out may be achieved across a wireless communication between the detector and imaging system. In this regard, one skilled in the art will appreciate that the imaging system and detector may be equipped with transceivers, antennas, and other operational circuitry to support the wireless transmission of data.

Figure 3:
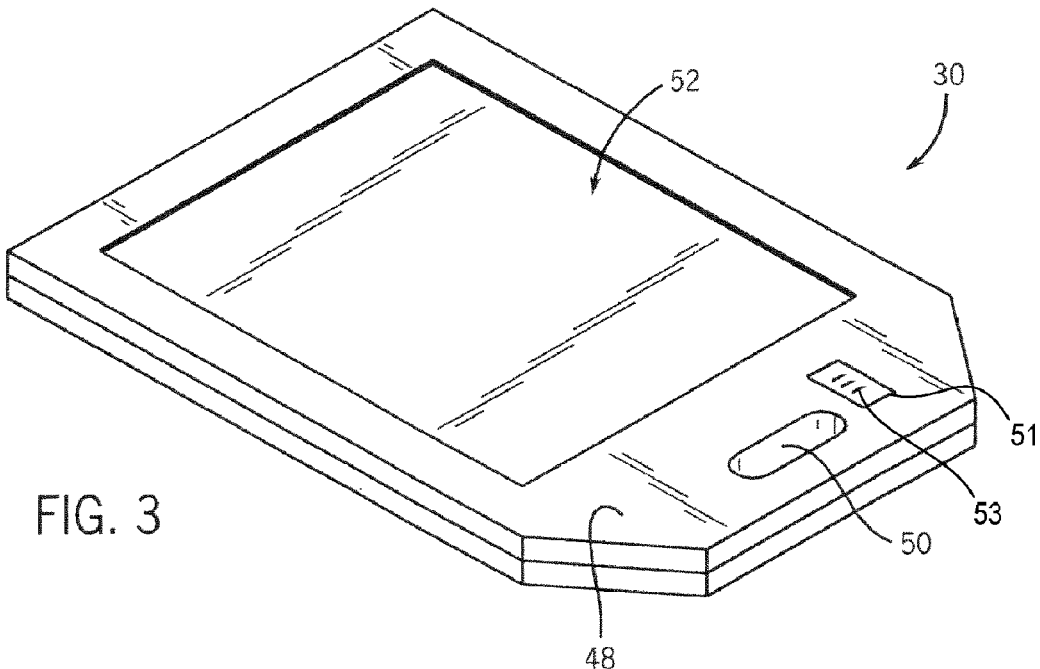
FIG. 3 is a perspective view of a portable, solid-state, flat panel, digital x-ray detector incorporating the present invention.

Referring now to FIG. 3, a perspective view illustrates a portable, flat panel x-ray detector 30 incorporating the present invention. Detector 30 is preferably an indirect detection, solid-state, digital detector that determines x-ray attenuation through an imaging subject from the emission of light by a scintillator that emits light upon the incidence of x-rays. The detector 30 includes a cover 48 formed of lightweight, durable composite material. A handle 50 is incorporated into the cover to support the portability of the detector. As shown, the detector 30 may be constructed without a fixed tether. In this regard, the detector may be connected to a tether (not shown), which is connected to the readout electronics when in use. When not in use, the detector may be easily detached from tether and stored remotely from the imaging system. The top of the cover includes a template 52 that visually defines the surface dimensions of the scintillator layer in the detector. Template 52 is designed to visually assist a user in positioning of the detector for data acquisition. The x-ray detector preferably includes an LED bank 51 that includes one or more LEDs 53 that may be illuminated to provide operational and/or diagnostic feedback.

While the present invention is particularly applicable with indirect detection digital detectors, the present invention may also be implemented with direct detection digital detectors. Direct detection digital detectors utilize a layer of amorphous selenium or a material of similar properties coupled to a thin film transistor array. X-ray interaction in the selenium layer releases electrons (or electron holes), which are used to form signal directly. An electrode is often used to create an electric field across the selenium layer to minimize the lateral spread of electrons, preserving spatial resolution. In addition to selenium, mercuric iodide, cadmium telluride, and lead iodide may be used.

Figure 4:
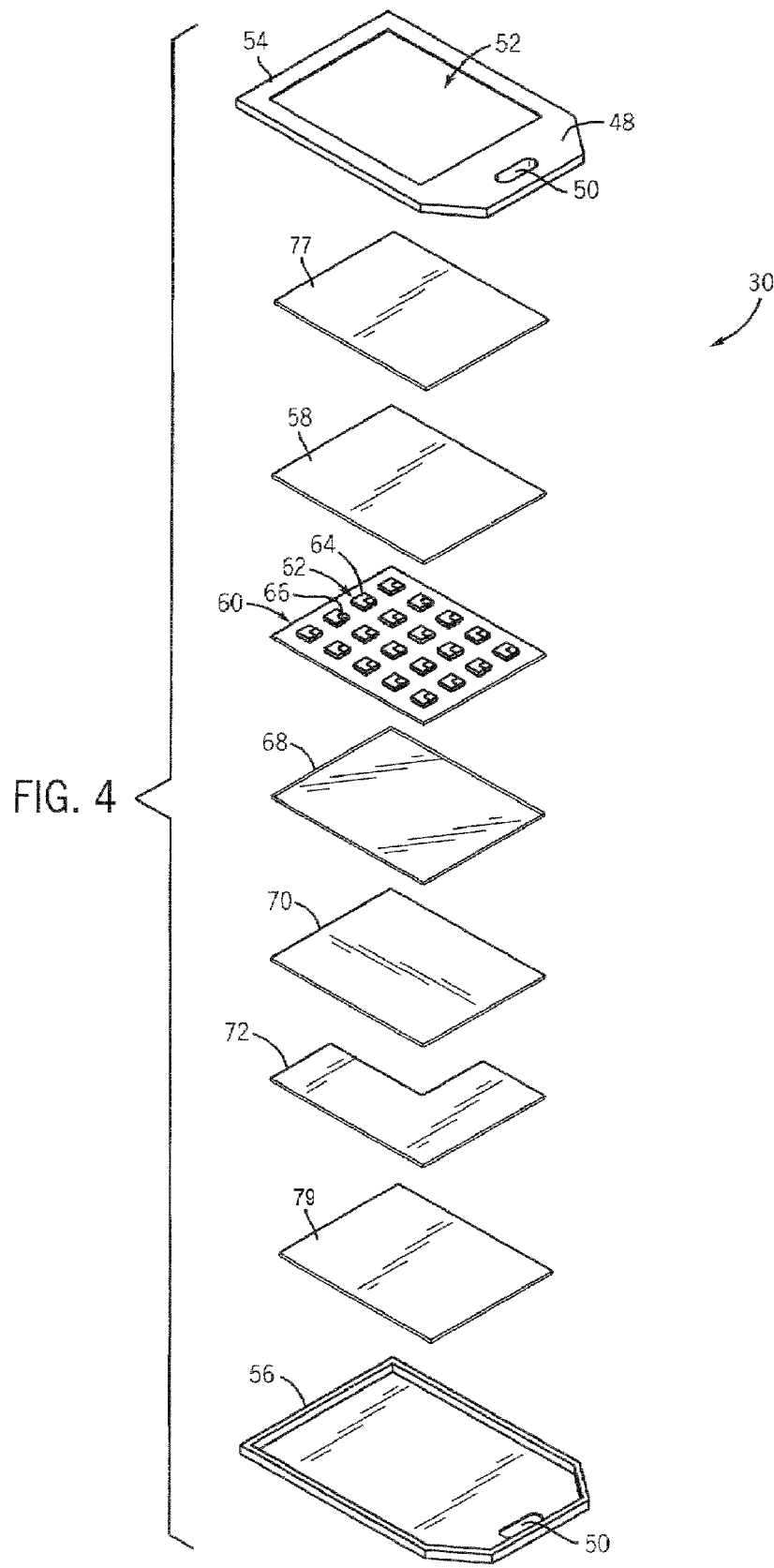
FIG. 4 is an exploded view of the x-ray detector shown in FIG. 3.

Referring now to FIG. 4, an exploded view schematically illustrates the internal composition of detector 30. Detector 30 includes a top cover 54 that along with base cover 56 provides a shell or enclosure for its internal components. Both covers 54, 56 are preferably formed of a composite material, such as carbon graphite, and impact-absorbing material, such as viscoelastic foam, so as to house and protect the detector components from fracture when exposed to a load or dropped. Covers 54 and 56 may be constructed with bumpers, foam inserts, layers of impact absorbing material, and the like to inhibit fracturing of the detector components when dropped or exposed to a load. When assembled, the top cover 54 is constructed in such a manner that the detector may be placed on a floor and used to support a standing subject. In this regard, the top cover panel 54 is designed to minimally deflect when subjected to a load.

Top cover 54 and base cover 56 collectively form handle 50 when assembled. The handle supports portability of the detector. Additionally, the detector is constructed to be quickly detached from a tether (not shown) that is used to connect the detector to the scanner during data acquisition and readout. That is, the detector may include a quick-connect connector or socket designed to receive a tether without requiring user access to an internal control panel of the detector. When un-tethered, detector 30 may be transported to and from multiple scan stations remote from one another. This is particularly advantageous for emergency rooms and other triage facilities. Further, the portability and detachability of the detector further enhances the mobility of a mobile x-ray imaging system, such as that shown in FIG. 1.

Detector 30 further includes a scintillator layer 58 designed to convert incident x-rays or gamma rays to visible light. Scintillator layer 58, which may be fabricated from CsI or other scintillating material, is designed to emit light proportional to the number and energy of the x-rays received. As such, light emissions will be higher in those regions of the scintillator layer 58 where either more x-rays were received or the energy level of the received x-rays was higher. Since the composition of the subject will attenuate the x-rays projected by the x-ray tube, the energy level of the x-rays impinging upon the scintillator layer will not be uniform across the scintillator layer. This variation in light emission will be used to capture contrast in the reconstructed image.

The light emitted by the scintillator layer 58 is detected by detector elements of a detector element array 60. Each detector element 62 corresponds to a picture element or pixel in the reconstructed image. Each detector element 62 includes a light sensitive or photoconductive region 64 and an electronics region 66. During exposure to x-rays, electrons are released in the light sensitive region 64 in proportion to the light detected in the region 64. The electronics region 66 includes a capacitor (not shown) that stores the electrical charge accumulated by the light sensitive region. After exposure, a thin-film-transistor (not shown) in the electronics region 66 is biased so as to connect the capacitor to readout electronics in the x-ray scanner. Generally, a multiplexer (not shown) is used to control read out of the discrete detector elements in a sequential, raster fashion. In this regard, the output of each detector element is sequentially input to a digitizer for digitization for subsequent image reconstruction.

The thin-film-transistors of the detector elements 62 are supported by a glass substrate 68. Lead lines (not shown) etched in substrate 68 are used for routing of the electrical output of the detector elements as well as applying the biasing voltages to the thin-film-transistors. The glass substrate is generally very thin and fragile. In this regard, as referenced above, the top cover 54 and base cover 56 are designed with impact absorbing material to help prevent fracturing of the glass substrate. Additionally, as the detector 30 may be used to support a relatively large load during imaging, e.g. imaging of the feet of an average sized adult male, the top cover panel 54 is further designed to reduce the stress on the detector to further prevent fracturing of the glass substrate and other detector components.

The glass substrate 68 is supported by a detector panel support 70. Panel support 70 is not only designed to support substrate 68, but is also used to separate the x-ray conversion and light detection components from motherboard 72. Panel support 70 is constructed to include radiation absorbing material in addition to structurally supporting material. Incorporating radiation absorbing material within the panel support reduces or eliminates the detection of backscattered x-rays. That is, the radiation absorbing material absorbs x-rays passing through the scintillator layer, detector element array, and glass substrate, as well as x-rays that deflect off the back cover of the detector. In this regard, the motherboard 72 is not imaged.

Motherboard 72, in one embodiment, has an L-shape and is disposed to support the processing and logic control electronics of the detector. The electronics preferably includes LEDs for monitoring operation and diagnostics of the detector. The electronics may also include temperature sensors for providing feedback as to the temperature of the detector as well as the temperature of the subject. As will be described, the electronics may also support one or more accelerometers or other gravitational force detectors designed to detect acceleration of the detector and store data accordingly. The accelerometer(s) may be sensitive to one or more dimensions, i.e. one, two, or three axes. In this regard, an accelerometer may be used to record the date and time when the detector experienced dramatic increases in acceleration, i.e. when dropped. The electronics may also include various storage devices including flash storage. In a wireless implementation, the electronics may include an antenna and transceiver for wirelessly transmitting data to the x-ray scanner. Additionally, the electronics may include a battery or other DC power source for powering the detector electronics. The electronics are supported by base cover panel 56.

As described above, the x-ray detector is designed to withstand relatively high-energy impacts, stresses, and strains such that the relatively sensitive components, i.e. scintillator layer, detector element array, glass substrate, and motherboard 72, are not damaged when the detector is dropped or stepped upon. In this regard, in one embodiment, the x-ray detector 30 includes two impact-absorbing layers 77, 79. One layer 77 is sealed against or otherwise placed in proximity to the undersurface of top cover panel 54 so as to be sandwiched between the top cover panel and scintillator layer 58. The other layer 79 is sealed or otherwise placed in proximity to the top surface of base panel 56 so as to be sandwiched between motherboard 72 and base panel 56. While two impact-absorbing layers 77, 79 are shown, it is contemplated that the detector may include only a single layer which is preferably sealed against the undersurface of top cover panel 54 or multiple layers interstitially disposed between the detector components. In this regard, the impact-absorbing material is designed not to attenuate radiation and, as such, does not interfere with data acquisition.

The impact-absorbing material is preferably a viscoelastic material that is designed to absorb the shock and vibrations placed on the detector when dropped but also deflect the force placed on the detector when stepped upon or otherwise subjected to a load, e.g. a standing patient for a foot/feet scan. In this regard, the impact absorbing material will deform when subjected to a load, but also recover its shape when the load is removed. As such, the impact-absorbing material has a memory.

The viscoelastic material, which may be foam or other plastic, is designed to deflect and absorb stresses and strains on the detector. As such, when the detector is stepped upon or dropped, the internal components of the detector, e.g. scintillator layer, detector element array, glass substrate, and motherboard, do not fracture or are otherwise damaged. One skilled in the art will appreciate that the thickness, density and composition of the impact-absorbing material may be variably selected to define the limits by which the detector may be subjected to a load or dropped without damage to the detector components. Preferably, however, the detector should have sufficient impact absorbing material such that the damage does not result when the detector is dropped a distance of 20 cm. and/or subjected to a point-load of 370 lbs.

Further, it is contemplated that layers 77 and 79 can have similar or dissimilar thicknesses, and be composed of similar or dissimilar impact absorbing material(s). For example, layer 77 may be designed to be more absorbent and deflective than layer 79. In this regard, layer 77 may be thicker than layer 79 or formed from material with improved absorption and deflective characteristics. Additionally, layer 77 may be formed of foam having pronounced viscoelastic properties whereas layer 79 is formed of a polycarbonate, PVC, or other material with less pronounced viscoelastic characteristics.

The present invention is a directed to a method and system of aligning an x-ray detector, such as that described with respect to FIGS. 3 and 4, relative to an x-ray tube of an x-ray scanner, such as that described with respect to FIG. 1, so that the x-ray detector and x-ray tube are properly spaced and oriented for data acquisition. As will be described in greater detail below, the x-ray detector and x-ray tube are equipped with transmitters and receivers designed to provide feedback relating to the orientation, spacing, and general position thereof. In this regard, a user can effectively and efficiently position the x-ray tube and x-ray detector relative to one another for data acquisition.

The invention includes the transmission of energy, preferably infrared light, toward sensors of an x-ray detector from a energy source at or near an x-ray tube. Alternatively, it is contemplated that energy may be transmitted from the x-ray detector toward one or more focal spots on the x-ray tube. Once the energy is received, it is processed to ascertain an orientation of the x-ray tube and x-ray detector with respect to one another and/or a distance between the x-ray tube and x-ray detector.

The energy transmitted in this system is not necessarily limited to infrared light, but can also include the entire visible spectrum of light, lasers, sound waves, radar, radio waves, microwaves, or any other energy form that is capable of being transmitted and detected. Infrared light is the preferred form of energy because of the inexpensive transmitters and receivers that are commercially available. Visible light can have a distinct advantage over infrared light in some applications; however, the transmitted energy can be used not only for position control but also as a visual feedback of the given orientation of the x-ray tube and the x-ray detector. The availability of inexpensive components for the infrared or visual light sensors makes these the preferred energy source for many applications. Other energy sources, such as laser energy may also be used. Laser beams would be an excellent choice as they provide higher resolution at greater distances. As the cost of components employed by alternate energy sources are reduced, these other forms of energy may become preferred. One skilled in the art will appreciate that sensors that detect infrared and laser forms of energy are generally classified as line-of-sight devices. However, the present invention is not limited to line-of-sight technology. It is contemplated that detecting the orientation of an x-ray detector and x-ray tube relative to one another may be achieved using sonar, GPS, and the like.

Figure 5:
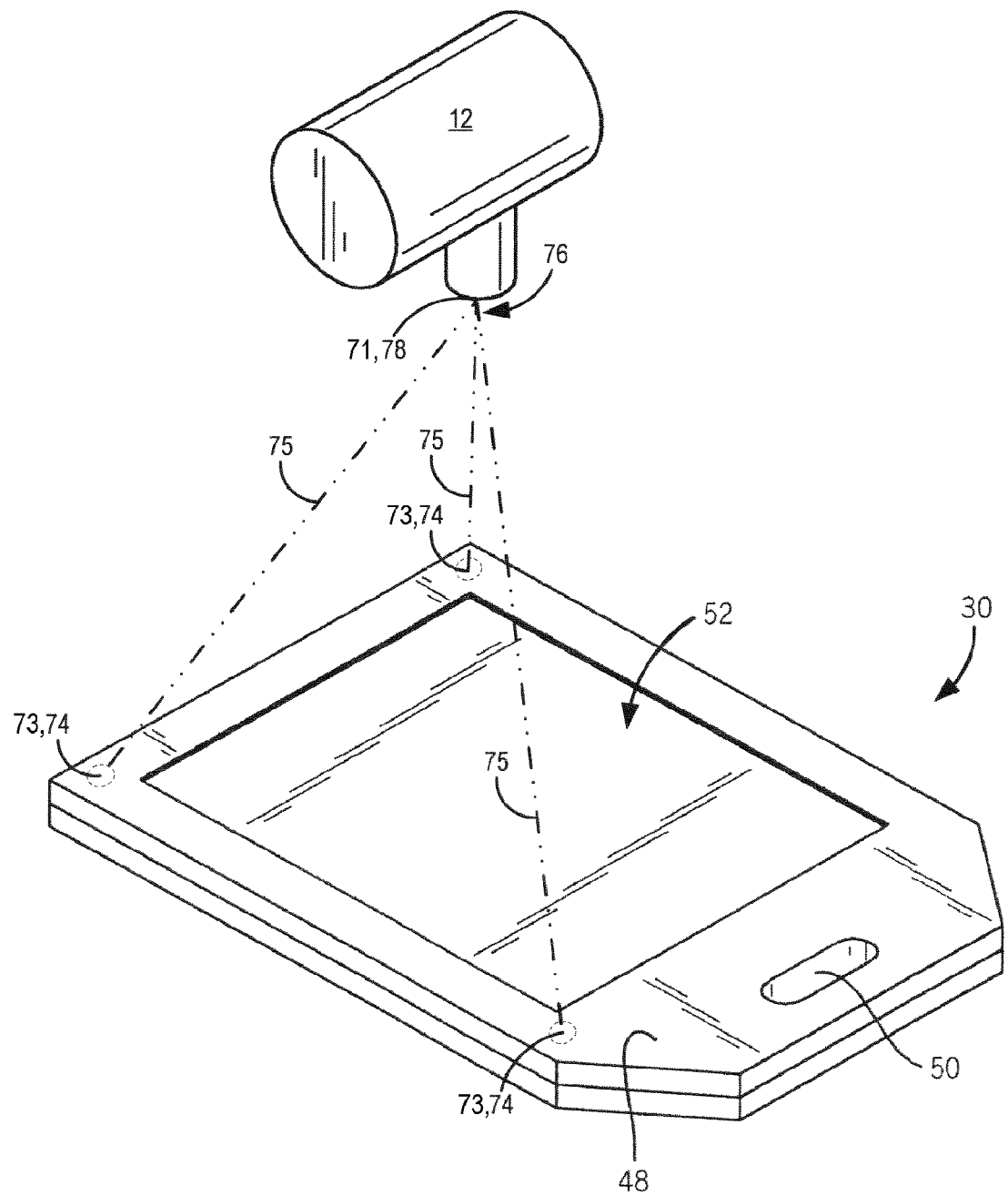
FIG. 5 is a perspective view of an x-ray tube relative to an x-ray detector illustrating alignment thereof in accordance with the present invention.

Referring now to FIG. 5, an x-ray tube 12 is shown relative to x-ray detector 30. X-ray detector 30 includes three energy sources 74, each designed to emit a beam 75 of energy toward x-ray tube 12. More particularly, the energy sources 74 are positioned such that the energy beams 75 intersect at a point of convergence or triangulation 76. The sources 74 are oriented in such a manner that the point of convergence 76 occurs at point centrally above the plane defined by the x-ray detector 30 and at a given distance thereabove. In this regard, when the x-ray tube is positioned at the point of convergence, the x-ray tube will emit x-ray energy for data acquisition centered about an axis perpendicular to the plane of the x-ray detector.

To determine when the x-ray tube is properly positioned relative to the x-ray detector, the x-ray tube includes a sensor 78 designed to receive the energy emitted by energy source 74. It is contemplated that a single sensor or multiple sensors may be used. If a single sensor is implemented, the amount of energy detected is processed to determine whether the x-ray tube and x-ray detector are properly positioned. That is, a known quantity of energy is emitted by the energy sources 74 of the x-ray detector. Accordingly, if the x-ray tube is properly positioned at the point of convergence, the intensity of the energy received by sensor 78 will be at a given magnitude. If the collective intensity of the energy received by sensor 78 is less this given magnitude, the x-ray tube and x-ray detector are deemed to not be properly aligned. As such, the x-ray detector and/or x-ray scanner may provide an audio and/or visual fault indicator indicating that proper positioning has not been achieved. Preferably, the point of convergence is set to a given height above the x-ray detector, if the collective intensity of the energy received the x-ray tube sensor 78 is at the given magnitude, it will be deemed that the x-ray tube is centrally positioned above the x-ray detector and is properly distanced from the x-ray detector as well.

It is also contemplated that the x-ray tube may be equipped with multiple sensors. In this regard, each sensor will detect energy from a corresponding energy source 74 of the x-ray detector 30. As such, when each of the multiple sensors detects energy emitted from energy sources 74, the x-ray detector and x-ray tube will be properly oriented with respect to one another. In this embodiment, proper positioning of the x-ray tube and x-ray detector will not be determined until each sensor intersects a corresponding energy beam 75 from the x-ray detector. Further to this embodiment, the intensity of the energy received by each sensor may be used to determine the distance of separation between the x-ray tube and x-ray detector. Accordingly, when the intensity is at a given value or within a given range, the x-ray detector and x-ray tube will be deemed to be properly spaced.

Referring again to FIG. 5, it is contemplated that the x-ray detector 30 may be equipped with sensors 73 and the x-ray tube may be equipped with one or more energy sources 71. In this embodiment, infrared or other energy sources at the x-ray tube 12, emit energy beams 75 at given angles relative to one another such that when each energy beam 75 is intercepted by an x-ray detector sensor 73, the x-ray detector and x-ray tube are properly aligned with one another. Each sensor 73 may provide feedback to the x-ray scanner or microcontroller in the x-ray detector regarding the detection of energy. Similar to the embodiments microprocessor discussed above, the intensity of the energy received may be processed to determine the amount of separation between the x-ray detector and the x-ray tube. It is preferred that the several energy beams 75 emitted by the x-ray tube be spaced and angled from one another in such a manner that all the energy beams 75 can only be simultaneously detected if the x-ray tube is centrally positioned above and with an x-ray beam path perpendicular to the x-ray detector.

Figure 6:
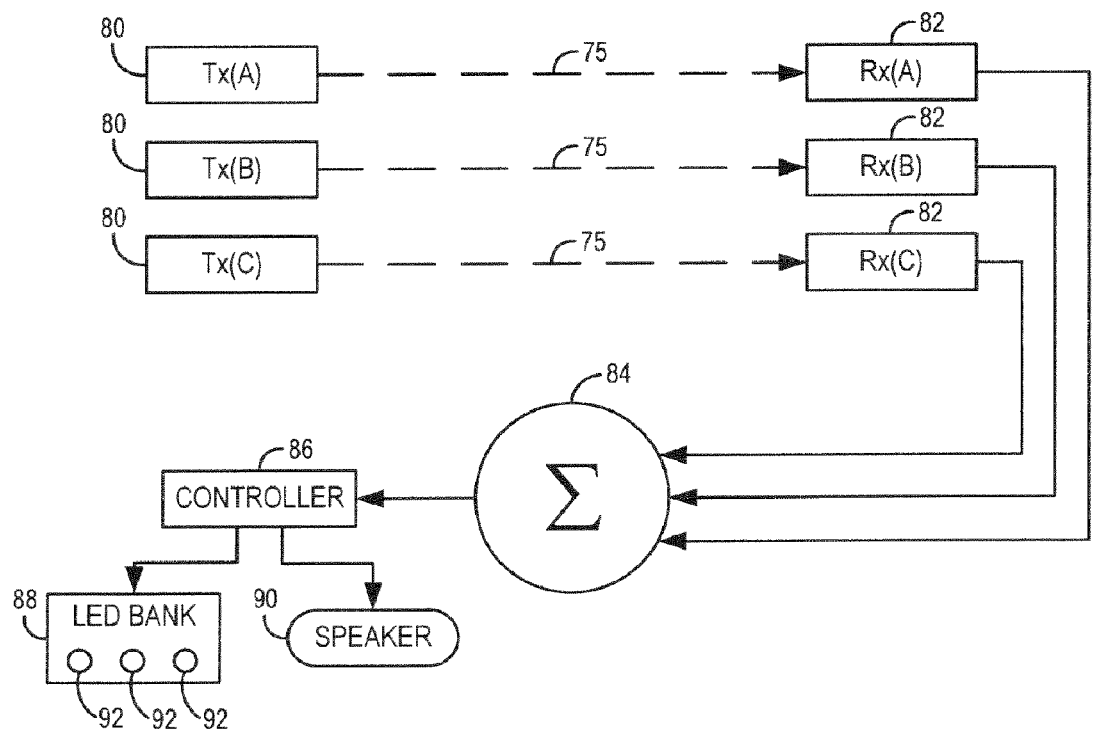
FIG. 6 is a schematic representation of an x-ray tube and x-ray detector alignment system in accordance with the present invention.

Referring now to FIG. 6, a block diagram illustrates one embodiment of the present invention. The x-ray detector/x-ray tube positioning system includes transmitters 80 designed to transmit energy toward receivers 82. The transmitters 80 may be integrated with the x-ray scanner or tube, and in which case the receivers 82 would be disposed in the x-ray detector. On the other hand, the transmitters 80 may be incorporated within or on the x-ray detector and the receivers located in or near the x-ray tube. In either embodiment, the energy impinged upon or otherwise detected by the receivers 82 is preferably sent to a summer, adder, or other computing component 84 whereupon the signals are processed such that a single input is provided to controller 86. In this regard, the controller determines the collective intensity of the energy detected by the receivers 82 and, from that collective intensity, determines whether the x-ray detector and x-ray tube are properly aligned and separated by a desired distance. It is also contemplated that the output of each sensor can be transmitted directly to controller 86.

For instance, each transmitter 80 is preferably constructed to emit a beam of energy at a given signal strength and at a given angle. In this regard, if the orientation between the x-ray detector and x-ray tube is not proper, the collective energy detected by the receivers will be below a threshold. Conversely, if the orientation is proper, the collective energy detected will exceed the threshold. Moreover, if the separation between the x-ray detector and the x-ray tube is less than desired, either the amount of energy received will exceed another threshold or, alternatively, the energy beams will not intersect the receivers. Accordingly, both distance and orientation information can be determined from the amount of energy received by the receivers 82.

It is also contemplated that audio and/or visual feedback may be provided to a user regarding orientation status of the x-ray detector and x-ray tube. As such, the present invention includes an LED bank 88 and a speaker 90. In one preferred embodiment, the LED bank 88 includes multiple LEDs 92. In this regard, a different LED is illuminated based upon the orientation of the x-ray detector and x-ray tube. For example, if an unacceptable orientation exists, a red LED is illuminated. If an acceptable, but not preferred orientation is reached a yellow LED is illuminated. And if a preferred orientation is reached, a green LED is illuminated. The controller 86 selectively causes illumination of the LEDs 92 depending upon the magnitude of energy detected by receivers 82. As described, the present invention includes an intermediary or "yellow" LED indicating to the user that an acceptable but not preferred orientation has been achieved. This can be particularly useful in emergency, triage facilities, and other time critical situations. For non-emergency circumstances, it is preferred that data acquisition not commence until the "green" LED is illuminated indicating that a preferred orientation between the x-ray tube and x-ray detector has been reached.

As mentioned, the system may also include a speaker 90 that provides an audio indicator of orientation status. This can be particularly helpful in those situations when the LED bank is obstructed from the view of the user. If the LED bank is incorporated into the x-ray detector, for a particular subject position, the LED may be difficult for a user to view. As such, the speaker can broadcast a chime or other audio signature indicating that an acceptable or preferred orientation has been reached. One skilled in the art will appreciate that the LED bank and speaker may be incorporated in the x-ray detector, x-ray scanner, or combination of both. It is also contemplated that messages providing a textual description of the orientation may be displayed on the x-ray scanner monitor or video console.

It is also contemplated that non-line-of-sight transmitters and receivers may be used, such as sonar, GPS, and the like. With GPS, for instance, the x-ray detector and x-ray tube may be equipped with GPS receivers that communicate with the Global Positioning System (GPS) of orbital satellites through radio waves. Through this communication, each GPS sensor can ascertain its global position. This information may then be readout and input to a processor in the x-ray detector or x-ray scanner to determine if the x-ray detector and x-ray tube are properly oriented with respect to one another. Further to this embodiment, it is contemplated that the global position information can be processed to provide feedback as to where the x-ray detector or x-ray tube should be repositioned to achieve the desired orientation. For instance, the x-ray tube may initially positioned and remain fixed in that position while a user positions the x-ray detector. Using GPS data from the x-ray detector, the processor can then not only determine that the x-ray detector has not reached a preferred position, but also determine the amount of error from the current detector position to the desired detector position. This error information can then be displayed on the x-ray scanner video console in a textual and/or graphical manner to assist the user in positioning the x-ray detector. One skilled in the art will appreciate that the same principles may be used to position the x-ray tube relative to a fixed x-ray detector. In this regard, the present invention is also applicable to fixed or stationary x-ray systems in addition to the mobile x-ray system illustrated in FIG. 1.

Therefore, the present invention includes an x-ray detector having a scintillator designed to output light in response to reception of x-rays and a detector element array configured to detect light output from the scintillator and output electrical signals indicative of the x-rays received by the scintillator for image reconstruction. The x-ray detector also has a plurality of electronic position sensors configured to provide feedback as to a position of the scintillator relative to an x-ray source.

Thee present invention also includes an x-ray imaging system. The system includes an x-ray source configured to provide a beam of x-rays at a subject to be imaged and a positionable x-ray detector configured to detect x-rays attenuated by the subject. The imaging system further includes a controller configured to electronically determine an orientation of the positionable x-ray detector relative to the x-ray source such that the positionable x-ray detector is substantially perpendicular to the beam of x-rays during imaging of the subject.

The present invention is also directed to an x-ray detector having means for converting x-rays into electrical signals capable of being processed for reconstruction of an image and means for electronically determining orientation of the converting means relative to an x-ray source such that the converting means is substantially perpendicular to an x-ray beam during data acquisition.

The present invention has been described in terms of the preferred embodiment, and it is recognized that equivalents, alternatives, and modifications, aside from those expressly stated, are possible and within the scope of the appending claims.

What is claimed is:

1. An x-ray detector comprising:
   a scintillator designed to output light in response to reception of x-rays;
   a detector element array configured to detect light output from the scintillator and output electrical signals indicative of the x-rays received by the scintillator for image reconstruction;
   a plurality of electronic position sensors; and
   a controller configured to receive and process feedback from the plurality of electronic position sensors and to determine, from the feedback, perpendicularity of a plane of the scintillator relative to an x-ray source.

2. The x-ray detector of claim 1 wherein the controller is further configured to provide one of an audio and a visual acknowledgement when the scintillator is positioned at a desired position relative to the x-ray source.

3. The x-ray detector of claim 2 wherein the controller is further configured to provide one of an audio and visual acknowledgement when the plane of the scintillator is at a position substantially perpendicular to the x-ray source.

4. The x-ray detector of claim 1 wherein the controller is further configured to emit an electronic signal at a point of triangulation defining a line of perpendicularity extending through a center of the plane of the scintillator.

5. The x-ray detector of claim 4 wherein the controller is further configured to provide one of an audio and a visual acknowledgment when the x-ray source is deemed positioned at the point of triangulation.

6. The x-ray detector of claim 1 wherein the plurality of electronic position sensors includes one of GPS sensors, line-of-sight sensors, and sonar sensors.

7. The x-ray detector of claim 6 wherein the line-of-sight sensors include infrared sensors.

8. The x-ray detector of claim 1 wherein the plurality of electronic position sensors includes three electronic sensors.

9. The x-ray detector of claim 1 wherein the controller is further configured to illuminate one or more LEDs based on the perpendicularity of the plane of the scintillator relative to the x-ray source.

10. The x-ray detector of claim 1 wherein the plurality of electronic position sensors is further configured to provide feedback as to a distance of a plane defined by the plurality of electronic position sensors from the x-ray source.

11. An x-ray imaging system comprising:
    an x-ray source configured to provide a beam of x-rays at a subject to be imaged;
    a positionable x-ray detector configured to detect x-rays attenuated by the subject;
    a plurality of sensors designed to receive feedback from at least one energy source; and
    a controller configured to process the feedback and to electronically determine, from the processed feedback, if a plane of the positionable x-ray detector is substantially perpendicular to the beam of x-rays during imaging of the subject.

12. The x-ray imaging system of claim 11 wherein the positionable x-ray detector includes the plurality of sensors.

13. The x-ray imaging system of claim 11 wherein the plurality of sensors includes one of:
    line-of-sight sensors;
    sonar sensors; and
    GPS sensors.

14. The x-ray imaging system of claim 13 wherein the line-of-sight sensors include infrared sensors.

15. The x-ray imaging system of claim 12 wherein the x-ray source includes the at least one energy source, wherein the at least one energy source is configured to emit a detectable signal toward the plurality of sensors of the positionable x-ray detector.

16. The x-ray imaging system of claim 13 wherein the controller is further configured to determine when the x-ray source is positioned at a point of reference and provide one of an audible and visual indication to a user when the x-ray source is deemed positioned at the point of reference.

17. The x-ray imaging system of claim 15 wherein the energy sources are configured to emit visible light.

18. The x-ray imaging system of claim 11 wherein the x-ray source and the positionable x-ray detector include GPS receivers designed to provide position data to the controller.

19. The x-ray imaging system of claim 11 wherein the positionable x-ray detector is a flat panel, solid state x-ray detector.

20. An x-ray detector comprising:
    means for converting x-rays into electrical signals capable of being processed for reconstruction of an image; and
    means for electronically determining orientation of the converting means relative to an x-ray source such that a plane of the converting means is substantially perpendicular to an x-ray beam during data acquisition.

21. An x-ray detector comprising:
    a scintillator designed to output light in response to reception of x-rays;
    a detector element array configured to detect light output from the scintillator and output electrical signals indicative of the x-rays received by the scintillator for image reconstruction;
    a plurality of electronic position sensors; and
    a controller configured to receive output from the plurality of electronic position sensors and triangulate a position of the scintillator.

* * * * *

UNITED STATES PATENT AND TRADEMARK OFFICE
CERTIFICATE OF CORRECTION

| | | |
|---|---|---|
| PATENT NO. | : 7,581,885 B2 | |
| APPLICATION NO. | : 10/904728 | |
| DATED | : September 1, 2009 | |
| INVENTOR(S) | : Jason R. Ertel | |

It is certified that error appears in the above-identified patent and that said Letters Patent is hereby corrected as shown below:

Title Page, Item [*] Notice:

The phrase "by 845 days" shall reflect as such appears on the Letters Patent.

Signed and Sealed this
Eighth Day of March, 2011

David J. Kappos
*Director of the United States Patent and Trademark Office*